United States Patent
Hannula

[11] Patent Number: 6,112,107
[45] Date of Patent: Aug. 29, 2000

[54] FLEXIBLE SENSOR WITH BULGE ENHANCING CONTACT

[75] Inventor: Don Hannula, San Luis Obispo, Calif.

[73] Assignee: Nellcor Puritan Bennett Incorporated, Pleasanton, Calif.

[21] Appl. No.: 09/203,648

[22] Filed: Dec. 1, 1998

Related U.S. Application Data

[63] Continuation of application No. 08/883,910, Jun. 27, 1997, abandoned, which is a continuation of application No. 08/647,817, May 15, 1996, abandoned.

[51] Int. Cl.[7] .......................................... A61B 5/00
[52] U.S. Cl. ........................................ 600/310; 600/323
[58] Field of Search ..................................... 600/309, 310, 600/322, 323, 340, 344, 382, 384, 391, 392, 473, 476; 250/216, 341.8, 339.12, 551

[56] References Cited

U.S. PATENT DOCUMENTS

| | | | |
|---|---|---|---|
| 4,865,038 | 9/1989 | Rich et al. | 600/344 |
| 5,237,994 | 8/1993 | Goldberger | 600/323 |
| 5,520,177 | 5/1996 | Ogawa et al. | 600/323 |
| 5,678,544 | 10/1997 | DeLonzor et al. | 600/344 |

*Primary Examiner*—Eric F. Winakur
*Attorney, Agent, or Firm*—Townsend and Townsend and Crew LLP

[57] ABSTRACT

A flexible sensor with strain relief on electrical contacts. Wires are attached to the electrical contacts, then a bulge of material is deposited over them, such as an adhesive. The wires are then bent back over the top of the bulge and secured. This prevents any tugging on the cable from pulling directly on the attachment of the wires to the contacts.

8 Claims, 8 Drawing Sheets

FLEXIBLE SENSOR WITH BULGE ENHANCING CONTACT

This application is a continuation of application Ser. No. 08/883,910, filed Jun. 27, 1997, now abandoned, which is a continuation of application Ser. No. 08/647,817, filed May 15, 1996, now abandoned, for SEMI-REUSABLE SENSOR WITH DISPOSABLE SLEEVE.

BACKGROUND OF THE INVENTION

The present invention relates to sensors for monitoring a patient, and in particular to disposable sensors used for oximetry.

Numerous types of sensors may detect various aspects of a patient's physiological condition. For example, temperature could be measured, blood pressure, heart rate, etc. Optical sensors can detect characteristics such as blood oxygen saturation by directing light into a patient and then detecting the scattered reflected or transmitted light. Additionally, Ph or other characteristics of the blood may be monitored. Pulse oximeter sensors also monitor the pulse waveform resulting from the heartbeat.

Oximetry sensors can typically either be reusable sensors mounted in rigid housing, such as a clip-on sensor, or can be disposable sensors mounted on a bandaid-type material. In the disposable sensors, it is desirable to have low cost manufacturing since they will be used only a single time. At the same time, reliability needs to be maintained.

U.S. Pat. Nos. 5,469,845 and 5,246,003, assigned to Nellcor Puritan Bennett, illustrate examples of a flexible sensor using a flex circuit which can be disposable. Typically, such a sensor would include an adhesive for attaching to a patient's skin, making the sensor necessarily disposable or raising sterilization issues.

One approach for reusing a flexible sensor is set forth in U.S. Pat. No. 5,090,410, assigned to Datascope Investment Corp. This patent sets forth a disposable sleeve into which a flexible sensor can be inserted, with the sleeve having adhesive for attaching to a patient. Thus, the relatively inexpensive sleeve can be thrown away with the sensor itself being reusable. This patent mentions the importance of ensuring that the sensor itself does not come in contact with either the patient, or an adhesive, to avoid the need for sterilization.

If a sensor designed for a single use is instead inserted into a sleeve and used multiple times, a number of operating issues arise. First, it is important that the sleeve allow the sensor to be properly attached in the manner in which it was intended. In addition, reliability issues may arise since a sensor designed to withstand wrapping around a patient's appendage a single time may break down if rewrapped several times. Accordingly, it is desirable to have an improved sleeve which would not impair a sensor's designed operation, and also a flexible sensor which is reusable.

SUMMARY OF THE INVENTION

The present invention provides an improved disposable sleeve for use with a sensor. The disposable sleeve includes two strips, and forms a pocket, with the pocket having an opening to receive the probe. A first adhesive is coupled to one of the strips for securing the sleeve to the patient. A second adhesive is placed on one of the strips at a position which can secure the probe in the pocket, while avoiding contact with the patient.

In one embodiment, the second adhesive is mounted on an interior surface of the pocket. A release liner covers the second adhesive, allowing the probe to be inserted into the pocket without being inhibited by the adhesive. After inserting and aligning the probe, the release liner can be removed. The release liner preferably is folded over near the closed end of the pocket so that when the free end is pulled, the liner separates from the closed end of the pocket first, enabling easy removal.

The present invention provides in one embodiment a disposable sleeve which includes a tab which can be folded over an end of the sensor to secure it in position. The tab insures that the sensor does not slip out or move around during use, thus varying the desired registration of the sensor with the sleeve and the patient. In one embodiment, the sleeve is adapted to receive an L-shaped sensor, with the tab being attached parallel to the main sleeve direction to wrap around the lower portion of the L-shaped sensor.

The present invention also provides in one embodiment features which enhance the durability of a flexible sensor, allowing multiple uses. Strain relief on electrical contacts is provided by attaching wires to electrical contacts, then depositing thereover a bulge of material, such as an adhesive. The wires are then bent back over the top of the bulge and secured. This prevents any tugging on the cable from pulling directly on the attachment of the wires to the contacts.

The present invention in one embodiment also mounts the sensing elements so that the contacts of the sensing element are orthogonal to the direction of bending of the flexible circuit. This also provides strain relief for the contacts by avoiding them being subjected to the same bending forces as if they were arranged in the typical prior art configuration of being in line with the direction of bending.

The present invention also provides in one embodiment an electromagnetic shield, or Faraday shield, which can be used with a flexible circuit. The Faraday shield will wrap around the flexible substrate to cover a light detector, with the shield itself then being sealed in with a covering layer.

For a fuller understanding of the nature and advantages of the invention, reference should be made to the following description taken in conjunction with the accompanying drawings.

DESCRIPTION OF THE PREFERRED EMBODIMENT

Figure 1A:
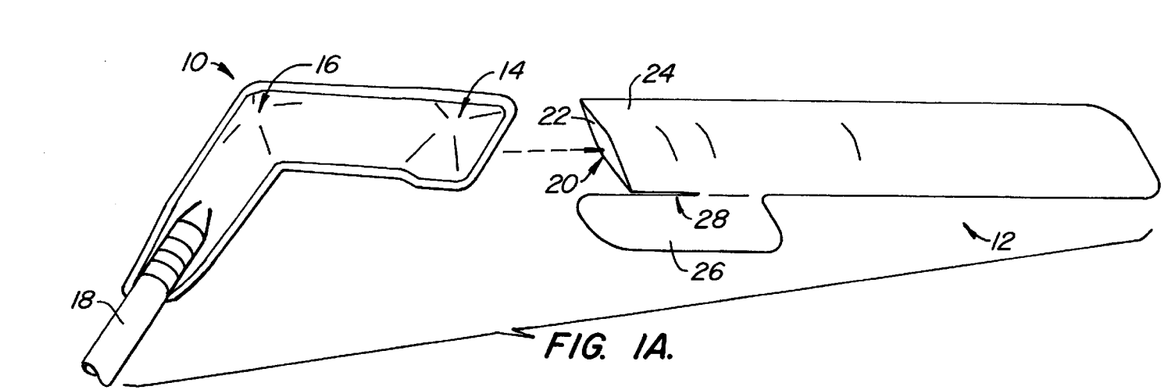
FIGS 1A–1C are diagrams illustrating a sensor inserted into a sleeve according to the present invention.

FIG. 1A shows a sensor 10 according to the present invention which can be inserted into a sleeve 12. Sensor 10 as shown is a pulse oximeter sensor having an emitter 14 and a detector 16 in sensor 10. The sensor is L-shaped, such that the portion holding emitter 14 can wrap around a patient's finger or other appendage, while the portion supporting a cable 18 can extend up the length of the appendage.

Sleeve 12 forms a pocket 20 between a bottom strip 22 and a top strip 24. Top strip 24 is transparent to allow light to pass through from the emitter and to the detector. A tab 26 is attached to the sleeve for securing the sensor as described below.

Figure 1B:
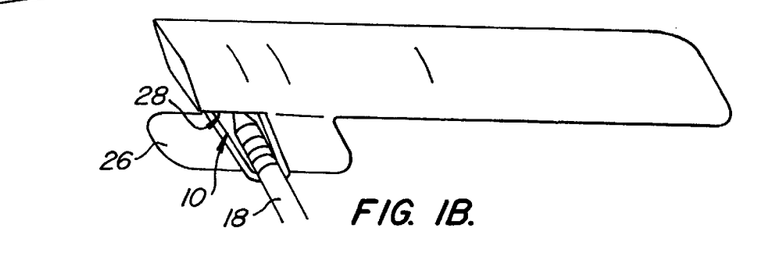

FIG. 1B illustrates sensor 10 inserted into sleeve 12 with cable 18 extending from the sleeve through a side slit 28. The end of the sensor connected to cable 18 extends over the top of tab 26.

Figure 1C:
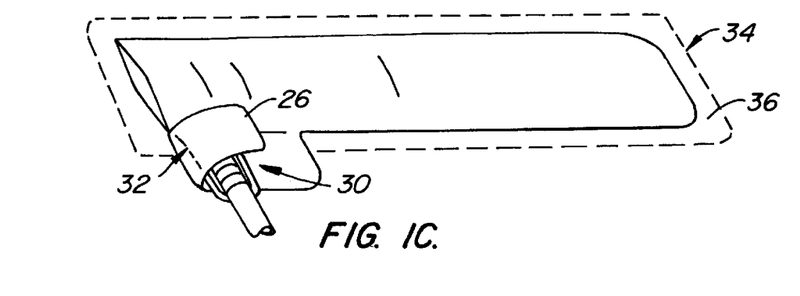

As illustrated in FIG. 1C, tab 26 is folded over the end of sensor 10 and secured to a far side 30 of the tab via an adhesive on the tab's surface. Thus, the sensor will be securely held in place so that it will not slip out of the sleeve or move about in the sleeve while being attached to a patient or while affixed to the patient.

In one embodiment, both strips 22 and 24 of the sleeve are transparent, with the sleeve being mounted on a backing 34. A surface 36 of the backing facing the sleeve can be made adhesive with this surface providing the adhesion of the combined sleeve and sensor assembly to a patient. The adhesive can also serve to secure the transparent sleeve by adhering to strip 22.

In an alternate embodiment, transparent top strip 24 has a transparent adhesive on it to allow it to be wrapped around an appendage of a patient and attach itself to the patient. When the assembly is removed from the patient, the sleeve can be simply thrown out, with the sensor then being reusable in a new sleeve. In one embodiment, tab 26 includes perforations 32 to allow the tab to be torn apart easily and the sensor 10 to be removed. In another embodiment, tab 26 is colored with a color, such as white, that allows it to be easily distinguished from the transparent sleeve 24.

Figures 2A, 2B:
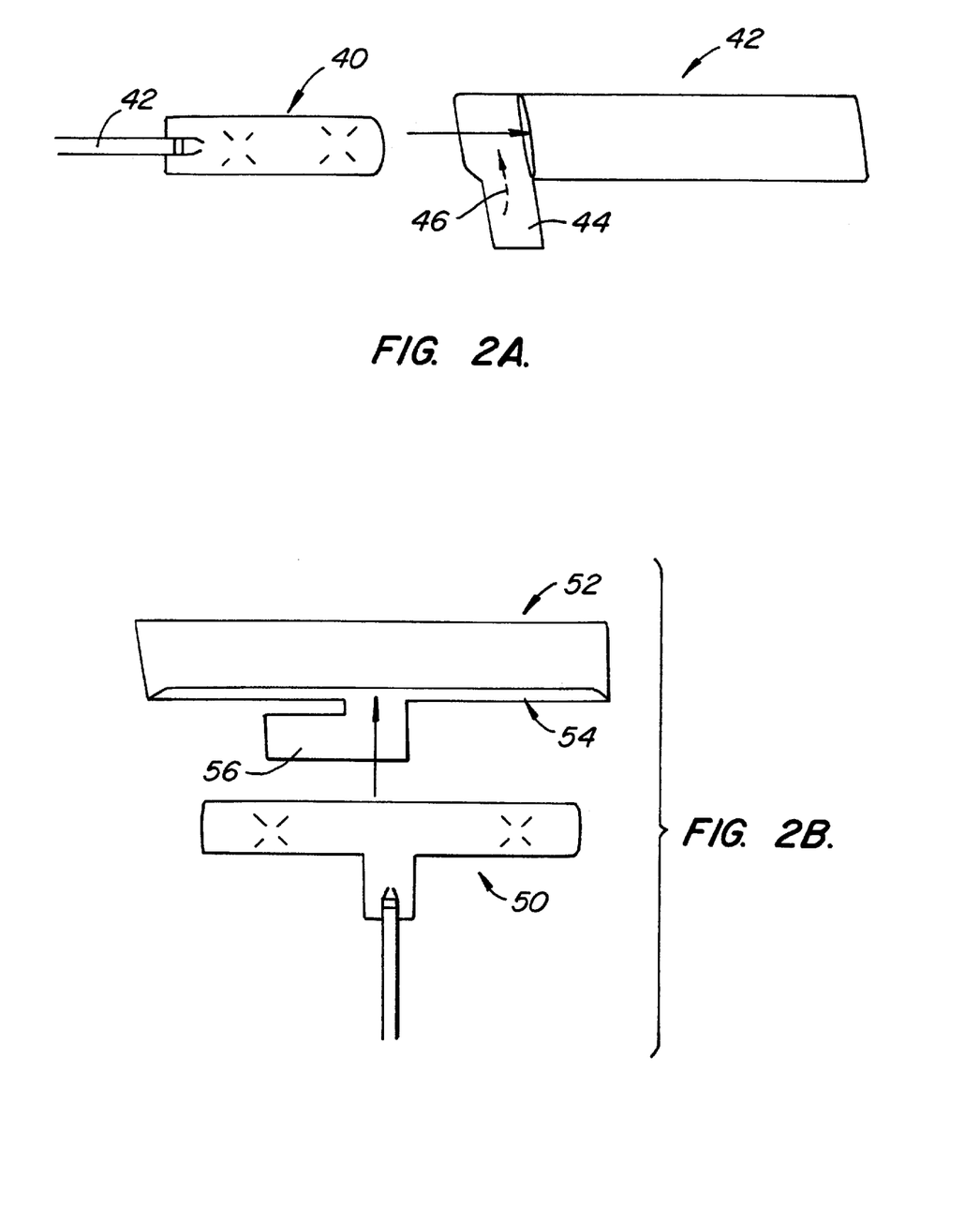
FIGS. 2A and 2B are alternate embodiments of a sleeve according to the present invention.

FIG. 2A illustrates an alternate embodiment of the invention in which a sensor 40 is not L-shaped, but rather in-line with a cable 42, and is inserted into a sleeve 42. Here, sleeve 42 includes a tab 44 which can be folded in the direction indicated by arrow 46 over cable 42 and the end of sensor 40 when it is inserted into sleeve 42.

FIG. 2B shows yet another embodiment, with a T-shaped sensor 50 which can be inserted into a correspondingly shaped sleeve 52. Sleeve 52 has an opening 54 along its length for allowing insertion of sensor 50. Alternately, an opening or a pair of slits could be included near the mid-portion of sleeve 52, with the sensor being secured by inserting first one leg and then the other. As shown, a tab 56 is attached to the sleeve which can be folded over the bottom portion of the T-shaped sensor 50 after insertion.

Figure 3:
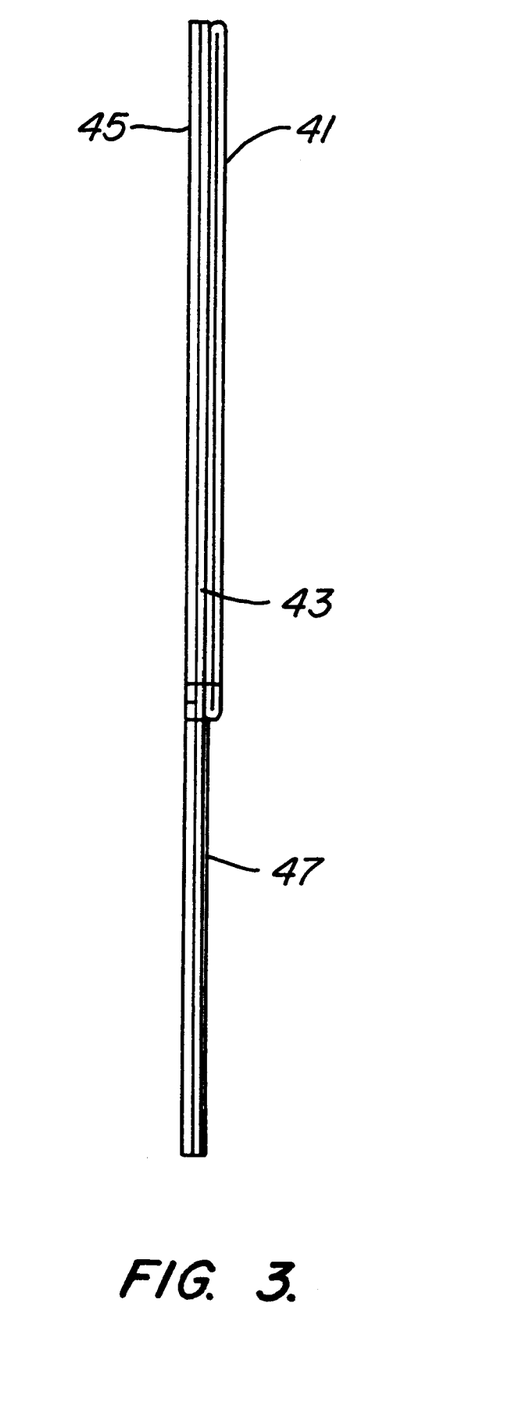
FIG. 3 is a side view of the multiple assembled layers of a sleeve according to the present invention.

FIG. 3 is a side view of the layers of a sheath according to the present invention, as finally assembled. First the tube 41 of the sheath itself is shown. This tube may be a white polyethylene or clear polyethylene, preferably with the thickness of between one half and four thousandths of an inch (0.0005"–0.004"). Tube 41 is held with an adhesive 43 to a release liner 45. Release liner 45 is preferably a paper liner with a silicone coating or another polyethylene sheath. A second release liner 47 covers the tab portion of the sheath.

During manufacturing, tube 41 could be formed by extruding the polyethylene. Alternatively, two polyethylene sheaths could be laser cut to the correct shape, with the laser cutting forming a seal as the cut is made.

Figure 4A:
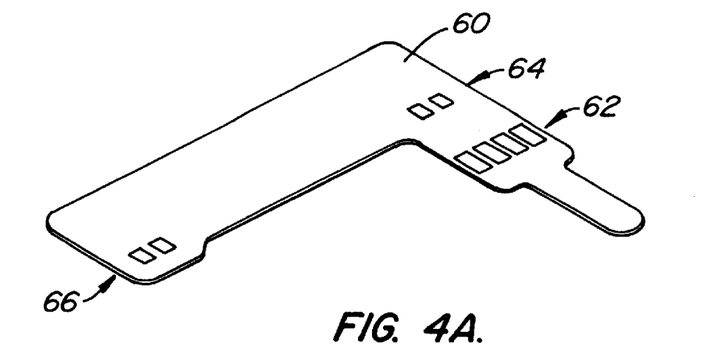
FIGS. 4A–4H are drawings illustrating the assembly process for a sensor according to the invention.

FIGS. 4A–4H illustrate the assembly of a sensor according to the present invention. In FIG. 4A, a substrate 60 (such as Kapton or polyimide) has a number of contacts 62, additional contacts 64 for an emitter, and contacts 66 for a detector.

Figure 4B:
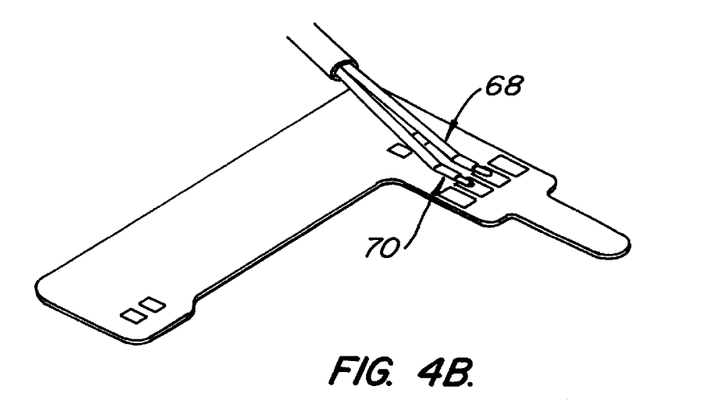
Figure 4C:
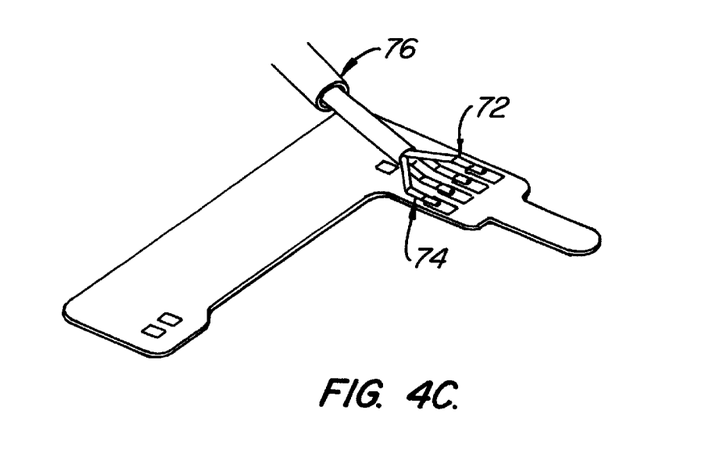

As shown in FIG. 4B, wires 68 and 70 are attached to the two middle contacts of the group of contacts 62. In FIG. 4B, outside wires 72 and 74 are then attached. It should be noted that the cable 76 enclosing the wires is extending in the opposite direction from the final, assembled direction.

Figure 4D:
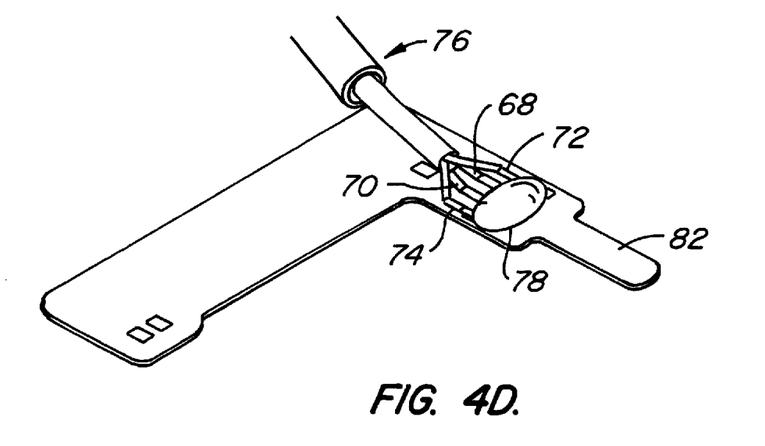

In 4D, a bulge of material 78 is placed over the contacts. The bulge can be an adhesive material, such as silicone adhesive. Alternately, a heat cured epoxy could be used or molded silicone could be used. The bulge 78 is preferably a UV adhesive, which is cured with a UV light source before bending the wires over it. Preferably, the bulge covers not only the contacts, but a portion of wires 68, 70, 72 and 74, especially any portion of the sensitive solder connection extending beyond the contact pads. The bulge serves two functions. It provides strain relief and also protects against electrical shorting between solder pads.

Figure 4E:
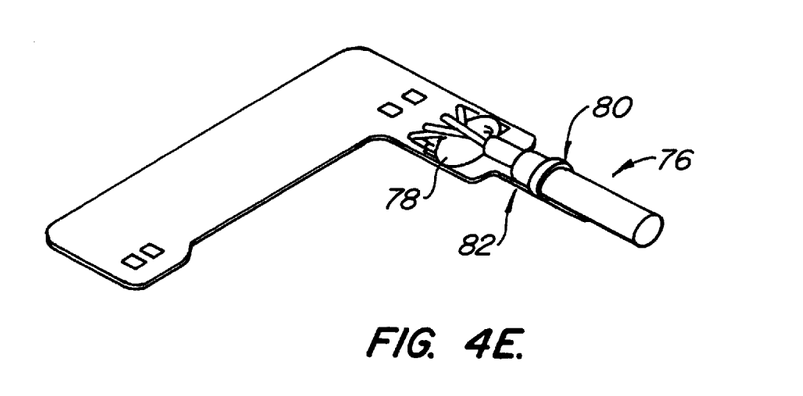

As shown in FIG. 4E, cable 76 is then bent back over the top of bulge 78 so that the wires bend across the top of the bulge. A clasp 80 is used to secure cable 76 to extending tab portion 82 of substrate 60. As can be seen, any pulling on the cable would not pull directly on the connection of the wires to the contacts. If a heat cured epoxy is used for bulge 78, after it adheres to the substrate, it is then cured before folding the wires over the top of it. An advantage of having bulge 78 extend beyond the contacts is that the solder used to attach the wires to the contact pads often extends past the pads, and is a likely place for breakage. By covering it with the bulge material 78, it is prevented from bending and thus breaking at this point.

Figure 4F:
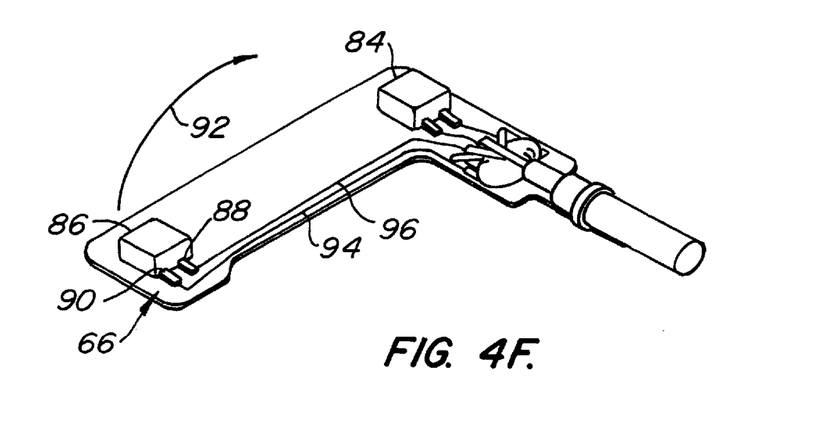

FIG. 4F illustrates the attachment of a photodetector 84 and photoemitter package 86. Package 86 would typically include both red and infrared LEDs for a pulse oximeter sensor. As can be seen, emitter package 86 includes a pair of leads 88 and 90, which are arranged at right-angles to a line between the emitter and detector. This prevents the leads from being bent significantly as the sensor is folded in a direction indicated by arrow 92 around a patient's appendage. In a typical prior art configuration, the leads would extend towards the detector simply for ease of laying out the conductive lines attaching to the leads. As shown in FIG. 4F, conductive lines 94 and 96 run the length of the substrate, and attach to the contacts 66. These lines will be subjected to bending forces as the sensor is bent along arrow 92. However, by arranging the leads 88 and 90 at an angle, the same bending forces are not imparted to the sensitive junction area. This promotes reliability over multiple uses of the sensor. The traces 94 and 96 would typically be a deposited copper film. Alternately, a copper-tin alloy could be used, or cadmium copper.

Figure 4G:
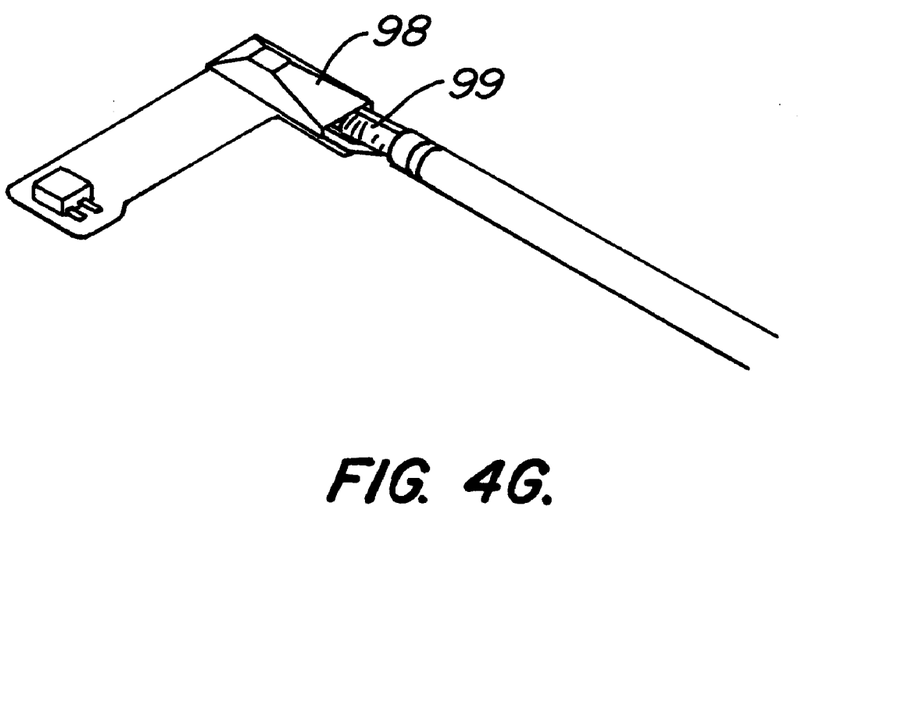
Figure 4H:
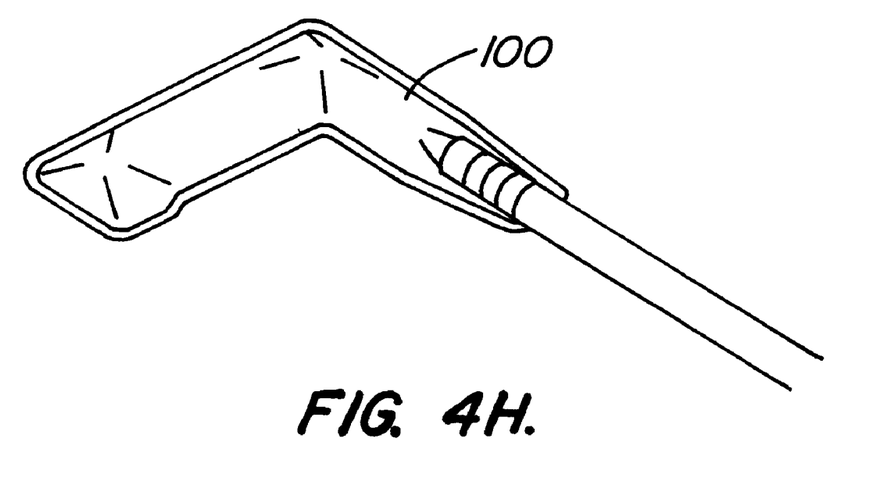

FIG. 4G shows a Faraday shield and covering 98 enclosed over the top of the detector 84, discussed in more detail below. In a preferred embodiment, the Faraday shield in layer 98 is soldered to a cable shield 99 to provide a ground connection. Finally, in FIG. 4H, a transparent sealing layer 100 is used to cover the top of the sensor. In one embodiment, film 100 is a white PVC film, which is either semi-transparent or has a clear PVC window over the emitter and detector.

Figure 5A:
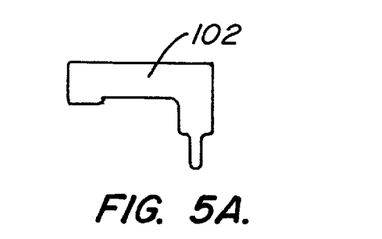
FIGS. 5A–5D illustrate the different layers of a flex circuit according to the invention.
Figure 5B:
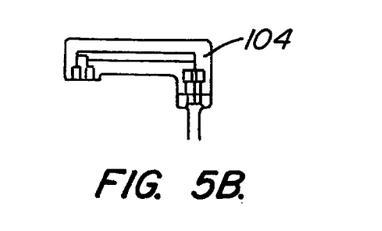
Figure 5C:
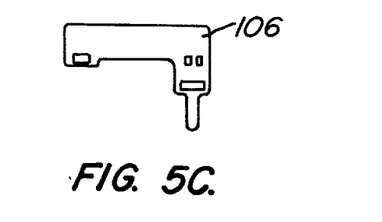
Figure 5D:
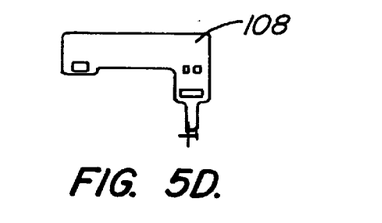

FIGS. 5A–5D illustrate the layers of the flex circuit used in the manufacturing process. FIG. 5A shows a first layer 102 forming the basic substrate, which may be made of a Kapton® film. Next, copper layer 104 is added to form the copper traces and contact pads. In one embodiment, a solid copper layer is placed over the Kapton® layer 102, and then etched away where copper is not desired as in a standard semiconductor manufacturing technique. Next, as shown in FIG. 5C, a layer 106 of Kapton® film covers the copper traces. Finally, a layer 108 may be added consisting of an adhesive which aids in the manufacturing process. The adhesive allows the emitter and detector illustrated in FIG. 4F to be mounted and remain in place while the soldering connections are made and the subsequent layers are deposited on it.

Returning to FIG. 4H, sealing layer 100 could be either a vinyl film or a urethane film. When the sealing is done in one embodiment, air is trapped inside sealing layer 100. Alternately, it may be sealed within a vacuum. This aids a subsequent sterilization process if it is desirable to sterilize the sensor after a use. A typical sterilization process will draw out the air with a vacuum during sterilization. An alternative to a vacuum seal would be a venting sealing layer, which as a hydrophobic layer. Such a layer would allow gas to pass, but not liquids. Thus, the sealing layer would not blow up with trapped air during sterilization.

Figure 6:
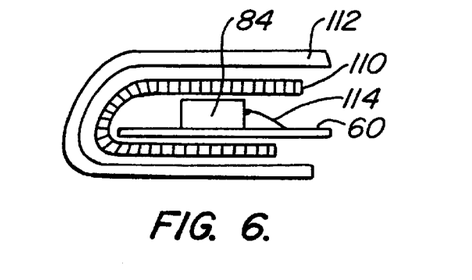
FIG. 6 is a side, cut-away view of an electromagnetic shield around a flexible sensor according to the present invention.

FIG. 6 illustrates the placement of a Faraday shield over a detector 84. As shown, detector 84 is mounted on substrate 60. A Faraday shield 110 wraps around from the bottom of substrate 60 around the edge and across the top. Subsequently, a layer 112 is used to seal the Faraday shield. In one embodiment, a vinyl seal is used. In one embodiment, only the portion of Faraday shield 110 above detector 84 need be a wire grid, with the bottom portion being solid. Alternately, a film with embedded conductive material could be used rather than a wire grid. Preferably, an underside of shield 110 is coated with an insulating layer to avoid it contacting leads 114 of the detector and shorting them out.

Figure 7:
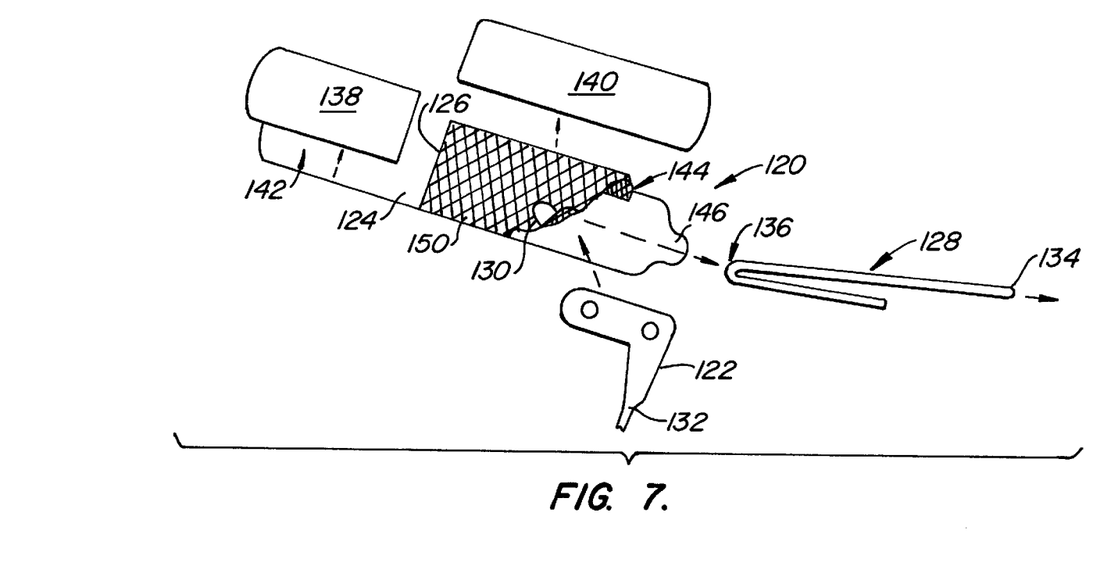
FIG. 7 is a perspective diagram of an embodiment of the sleeve with the adhesive inside the pocket and a release liner.

FIG. 7 illustrates an embodiment of a sleeve 120 for accepting an L-shaped sensor probe 122. Sleeve 120 includes a first strip 124, onto which is mounted a second strip 126. First strip 124 has an adhesive on its surface facing the interior of the pocket formed between it and strip 126. The adhesive is initially covered with a release liner 128.

Probe 122 is inserted into the pocket while release liner 128 is in place, so that the release liner allows probe 122 to smoothly slide into the pocket without becoming stuck to the adhesive and preventing sliding into position. A tab 130 is used to give a user a visible indicator and a means for opening the pocket after use. This helps the user open the wrap correctly in order to avoid damaging the sensor. Preferably, tab 130 may be colored, such as with blue, to distinguish it from the substantially transparent strip 126.

After probe 122 is inserted and in place, release liner 128 can be removed by pulling on end 134. This will apply pressure first to the folded portion 136, allowing it to be peeled away from the adhesive easily.

Additional release liners 138 and 140 are mounted over the other adhesive portions. In particular, release liner 138 is over an adhesive portion 142 of strip 124, while release liner 140 is placed over the adhesive top surface of strip 126. Preferably, in mounting, strip 126 is folded over slightly so that its adhesive side contacts strip 124 at point 144 near the edge of strip 124. Strip 124 includes a tab 146 without an adhesive surface. This tab allows grasping by a user for placement of the sleeve on a patient. Adhesive surfaces 142 and the top of strip 126 are applied to the patient.

Figure 8:
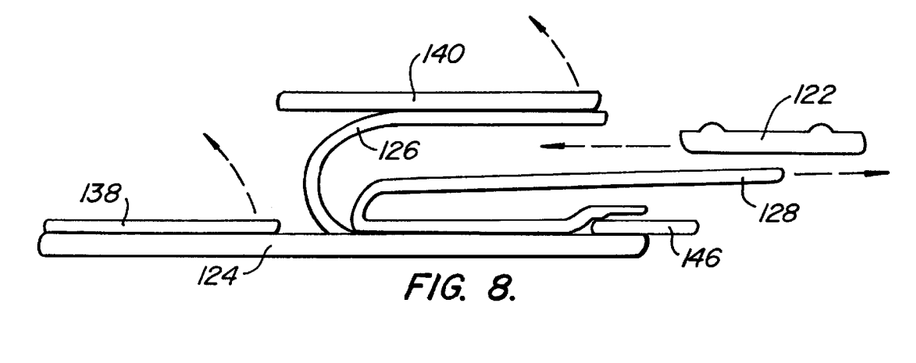
FIG. 8 is a side, cutaway view of the embodiment of FIG. 7.

FIG. 8 shows a cutaway view of the sleeve of FIG. 7 which is exaggerated to illustrate the operation of the invention.

As can be seen in FIG. 7, strip 126 preferably includes a reinforcing mesh 150. Preferably, mesh 150 is white thread material. The mesh performs two functions. First, it provides a reinforcing function, making the strip easier to handle, thus making the sleeve easier to manufacture. In addition, it can perform a shunt blocking function, preventing light from otherwise shunting through transparent strip 126 from the emitter to the detector of the probe. The weave of the mesh has sufficient spacing to allow light to be emitted from and detected by the probe without significant impairment. Mesh 150 is attached to strip 124 along its top edge, its left edge, and about two-thirds of its bottom edge.

The release liners can be silicone-coated in order to facilitate release during removal of the liner. The release liners can include a pull-tab which may be opaque or printed to provide visual feedback to the user. In addition, assembly instructions can be printed on of the release liners to show the users which steps to follow. For instance, release liner 140 can have printed on it a number 1 with an arrow indicating the insertion of the probe, and a number 3 indicating the removal of the release liner after release liner 128 has been removed. Release liner 128 can have an arrow indicating it should be pulled out, with the number 2 indicating it should be pulled out after the probe has been properly placed in accordance with step 1.

The adhesives of the embodiments of the present invention function to immobilize the sensor probe when attached to the patient. This immobilization minimizes motion artifact due to the slippage of the probe in the sleeve, which would affect the signal detected.

As will be understood by those skilled in the art, the present invention may be embodied in other specific forms without departing from the spirit or essential characteristics thereof. Accordingly, the above description is meant to be illustrative, but not limiting, of the scope of the invention, which is set forth in the following claims.

What is claimed is:

1. A sensor comprising:
   a flexible substrate;
   a sensing element mounted on said substrate;
   at least one contact on a first side of said substrate, said contact being connected to said sensing element;
   a bulge extending from said substrate adjacent said contact; and
   a cable connected to said contact, extending away from said bulge, and then bending back over said bulge.

2. The sensor of claim 1 wherein said bulge comprises an adhesive.

3. The sensor of claim 1 wherein said bulge is mounted over said contact.

4. The sensor of claim 1 wherein said bulge extends partially over said cable beyond said contact.

5. The sensor of claim 1 wherein said bulge is a UV adhesive.

6. The sensor of claim 1 wherein said substrate is a flexible substrate capable of curving in a first direction at least partially around the skin of a patient, and further comprising:
   at least one conductor extending at least partially along said first side of said substrate; and
   at least one conductive lead connecting said sensor element to said conductor, said lead extending from said sensor element to said conductor in a second direction at an angle to said first direction.

7. The sensor of claim 1 wherein said sensing element is a light detector, and further comprising an electromagnetic shield having at least a first portion being light penetrable and conductive, said shield being folded around from a second side of said substrate to said first side so that said first portion covers said light detector.

8. The sensor of claim 1 further comprising an adhesive layer between said substrate and said sensing element.

* * * * *